(12) United States Patent
Comings et al.

(10) Patent No.: US 6,395,488 B1
(45) Date of Patent: May 28, 2002

(54) CHOLECYSTOKININ (CCK) GENE AS A RISK FACTOR FOR SMOKING IN WOMEN

(75) Inventors: David E. Comings, Duarte; James P. MacMurray, Loma Linda, both of CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/559,917

(22) Filed: Apr. 28, 2000

(51) Int. Cl.$^7$ .............................. C12Q 1/70; C12P 19/34
(52) U.S. Cl. ......................... 435/6; 435/91.1; 435/91.2; 536/23.1
(58) Field of Search ......................... 435/6, 91.1, 91.2; 536/23.1

(56) References Cited

U.S. PATENT DOCUMENTS 5,650,282 A * 7/1997 Keating et al. ................. 435/6

OTHER PUBLICATIONS

Chowhury, P., et al., "Structural and Functional Changes of Rat Exocrine Pancreas Exposed to Nicotine," *International Journal of Pancreatology*, (1995), vol. 18, No. 3, pp. 257–264.

Doi, R., et al., "Carbachol and Cholecystokinin Enhance Accumulation of Nicotine in Rat Pancreatic Acinar Cells," *Pancreas*, (1995), vol. 10, No. 2, pp. 154–160.

Fuxe, K., et al., "Acute Continuous Exposure to Cigarette Smoke Produces Discrete Changes in Cholecystokinin and Substance P Levels in the Hypothalamus and Preoptic Area of the Male Rat," *Acta Physiol. Scand*, (1985), vol. 125, No. 3, pp. 437–443.

Harada, S., et al., "A New Genetic Variant in the Sp1 Binding Cis–Element of Cholecystokinin Gene Promoter Region and Relationship to Alcoholism," *Alcoholism: Clinical and Experimental Research*, (1998), vol. 22, No. 3, pp. 93S–96S.

Ishiguro, H., et al, "No Association Between C–45T Polymorphism in the Sp1 Binding Site of the Promoter Region of the Cholecystokinin Gene and Alcoholism," *Psychiatry Research 85*, (1999), pp. 209–213.

Nielsen, F., et al., "Transcriptional Regulation of the Human Cholecystokinin Gene: Composite Action of Upstream Stimulatory Factor Sp1, and Members of the CREB/ATF–AP–1 Family of Transcription Factors," *DNA and Cell Biology*, (1996), vol. 15, No. 1, pp. 53–63.

Noble, F., et al., "CCK–B Receptor: Chemistry, Molecular Biology, Biochemistry and Pharmacology," *Progress in Neurobiology*, (1999), vol. 58, pp. 349–379.

Okubo, T., et al. "Genetic Association Between Alcohol Withdrawal Symptoms and Polymorphism of CCK Gene Promoter," *Alcoholism: Clinical and Experimental Research*, (1999), vol. 23, No. 4, pp. 11S–12S.

Rasmussen, K., et al., "The CCK–B Antagonist LY288513 Blocks the Effects of Nicotine Withdrawal on Auditory Startle," *Auditory and Vestibular Systems, Lateral Line*, Neuroreport, (1996), vol. 7, pp. 1050–1052.

Tachikawa, H., et al., "Novel Polymorphism in the Promotoer and Coding Regions of the Human Cholecystokinin B. Receptor Gene: An Association Analysis with Schizophrenia," *Am. J. Med. Genet.*, (1999), vol. 88, vol. 6, pp. 700–704.

Wang, Z., et al., "Possible Association of a Cholecystokinin Promoter Polymorphism ($CCK_{-36CT}$) with Panic Disorder," *Am. J. Med. Genet.*, (1998), vol. 81, pp. 228–234.

\* cited by examiner

*Primary Examiner*—Jeffrey Fredman
*Assistant Examiner*—Juliet Einsmann
(74) *Attorney, Agent, or Firm*—Rothwell, Figg, Ernst & Manbeck

(57) ABSTRACT

The present invention is directed to the C-45T polymorphism in the Sp1 binding region of the CCK gene and the role of genetic variants in the CCK gene as a risk factor for smoking and/or unsuccessful smoking cessation in women. In particular, the invention is directed to a method for diagnosing a polymorphism which is a risk factor for smoking comprising hybridizing a nucleic acid probe, which hybridizes specifically to an isolated DNA comprising a nucleotide sequence coding for human CCK containing a polymorphism described herein or its complement, to a patient's sample of DNA or RNA under stringent conditions which allows hybridization of said probe to nucleic acid comprising said polymorphism but prevents hybridization of said probe to a wild-type nucleic acid, wherein the presence of a hybridization signal indicates the presence of said polymorphism.

8 Claims, 2 Drawing Sheets

CHOLECYSTOKININ (CCK) GENE AS A RISK FACTOR FOR SMOKING IN WOMEN

This application was made with Government support under Grant No. 911431 funded by the National Institutes of Health, Bethesda, Md. The federal government may have certain rights in this invention.

BACKGROUND OF THE INVENTION

The present invention is directed to the C-45T polymorphism in the Sp1 binding region of the cholecystokinin (CCK) gene and the role of genetic variants in the CCK gene as a risk factor for smoking and unsuccessful smoking cessation in women.

The publications and other materials used herein to illuminate the background of the invention or provide additional details respecting the practice, are incorporated by reference, and for convenience are respectively grouped in the appended Lists of References.

Despite knowledge of the potential consequences, after a decade of a decrease in the percent of the U.S. population that smokes, the decline has leveled off at about 25 percent. See Centers for Disease Control and Prevention, (1995 Report); Giovino et al. (1995); and Kendrick and Merritt, 1996. Approximately half of smokers are women, and women find it particularly difficult to stop smoking because of fears of gaining weight. See Crisp et al., 1999; Klesges et al., 1999; and Sorensin and Pechacek, 1987. The identification of the mechanism by which nicotine influences appetite could lead to the identification of more effective smoking cessation programs, especially in women. In this regard CCK regulates weight by producing a feeling of satiety (Smith and Gibbs, 1994), and animal studies show that both accurate and chronic exposure to nicotine results in increased plasma CCK levels and weight loss (Chowdhury et al., 1989; Chowdhury et al., 1991; and Winders and Grunberg, 1989). The weight loss is associated with a decrease in food intake and an increase in metabolism, as well as decreases in plasma glucose and insulin levels (Chowdhury et al., 1990; Crawley and Corwin, 1994). Cholecystokinin (CCK), one of the most abundant neuropeptides in the brain, plays a role in a wide range of behaviors in addition to feeding including learning, memory, anxiety, pain, drug dependence and withdrawal. See Costall et al., 1991; Crawley and Corwin, 1994; Fink et al., 1999. Rasmussen et al. (1996) reported that a CCK antagonist significantly decreased the symptoms of nicotine withdrawal in animals.

The identification of a C-45T polymorphism in the Sp1 binding cis-element of the CCK gene (Harada et al. 1998) has allowed the investigation of the role of CCK variants in various human behaviors. Harada et al. (Harada et al. 1998) reported a significant increase in the frequency of the T allele in Japanese alcoholics compared to controls, but this was not replicated in Japanese in a study by Ishiguro et al. (Ishiguro et al. 1999). Studies of a C-36T mutation, also in the Sp1 binding region, have suggested a role of the CCK gene in panic disorder in some (Wang, et al. 1998) but not all (Kennedy et al. 1999) studies. Based on the above observations we hypothesized that the T allele of the C-45T polymorphism of the CCK gene might be associated with BMI (Body Mass Index) and/or smoking in women, and might provide insights into the role of smoking in weight control. Other polymorphisms of the CCK gene, e.g., the C-36T polymorphism, might also be associated with BMI and/or smoking in women, and might provide further insights into the role of smoking in weight control. Because the T allele of the C-45T polymorphism of the CCK gene may be associated with smoking in women, genetically defective CCK genes could play an important role as a risk factor determinant for nicotine dependence and unsuccessful cessation thereof.

Thus, there is a continued need to investigate genes involved in the neuropathways of the brain to identify risk factors for smoking and markers for a genetic predisposition to problems with smoking cessation which can be used for diagnosis of the above-described disorders and for guiding drug therapy, e.g., for the identification of agents which may be useful aids for smoking cessation.

SUMMARY OF THE INVENTION

The present invention is directed to the C-45T polymorphism in the Sp1 binding region of the CCK gene and the role of genetic variants in the CCK gene as a risk factor for smoking and unsuccessful smoking cessation in women. In particular, the present invention is directed to the discovery that 12.3% of women who never smoked carried the T allele. Carriers of the T allele increased to 26.8% for women who had smoked but had stopped, and to 75% for women who were unable to quit smoking ($p \leq 0.00009$). Using the discovery of the present invention, CCK acting agents are useful aids for smoking cessation. Now that the C-45T polymorphism of the CCK gene has been discovered, gene libraries can be searched for other polymorphisms that are in linkage disequilibrium with the one shown.

In a one aspect, the present invention is directed to the role of genetic variants in the CCK gene as a risk factor for smoking and unsuccessful smoking cessation in women.

In a second aspect of the invention, analysis of the T allele of the C-45T polymorphism of the CCK gene is provided for diagnosis of subjects to identify women who will be candidates for CCK acting smoking cessation agents. The diagnostic method comprises analyzing the DNA sequence of the CCK gene for the presence of the C-45T polymorphism of an individual to be tested and comparing it with the DNA sequence of the native, non-variant genes. In a second embodiment, the CCK gene of an individual to be tested is screened for polymorphisms associated with smoking in women. The ability to predict an inability of a subject to quit smoking will enable physicians to treat such disorders with appropriate medical therapies.

In a third aspect of the present invention, the polymorphisms in the CCK gene are used for drug screening and testing.

In a fourth aspect of the present invention, the CCK gene is analyzed for other polymorphisms associated with smoking.

In a fourth aspect of the present invention, gene libraries are searched for other polymorphisms that are in linkage disequilibrium with the C-45T polymorphism.

DETAILED DESCRIPTION OF THE INVENTION

The present invention is directed to the C-45T polymorphism in the Sp1 binding region of the CCK gene and the role of genetic variants in the CCK gene as a risk factor for smoking and unsuccessful smoking cessation in women.

Subjects. As part of a study of the genetics of obesity we advertised for women who were overweight to participate in a study of weight control. The women who agreed to participate were asked to bring a non-obese female friend of comparable age, socioeconomic and ethnic background as a control. While the emphasis in this study was on the genetics of obesity, questions were also asked about whether the subjects had ever smoked, had smoked but stopped or were current smokers. Other assessments included the SCL-90 for the evaluation of symptoms of depression and anxiety (Steer et al. 1994). All subjects in the present study were non-Hispanic Caucasians.

Genotyping. The C-45T polymorphism of the CCK gene (Harada et al. 1998) was used in conjunction with the PCR conditions described herein. In particular, restriction enzymes were utilized to produce restriction fragments which were then amplified using PCR. Detection of target sequences was facilitated by gel electrophoresis.

Statistics. The association of the CCK genotypes with smoking status was assessed by Pearson chi square analysis. The potential role of age, anxiety and depression as confounding variables was assessed by ANOVA using smoking status as the dependent variable, CCK genotypes (CC vs CT), age, and SCL-90 anxiety and SCL-90 depression scales as covariates.

Figure 1:
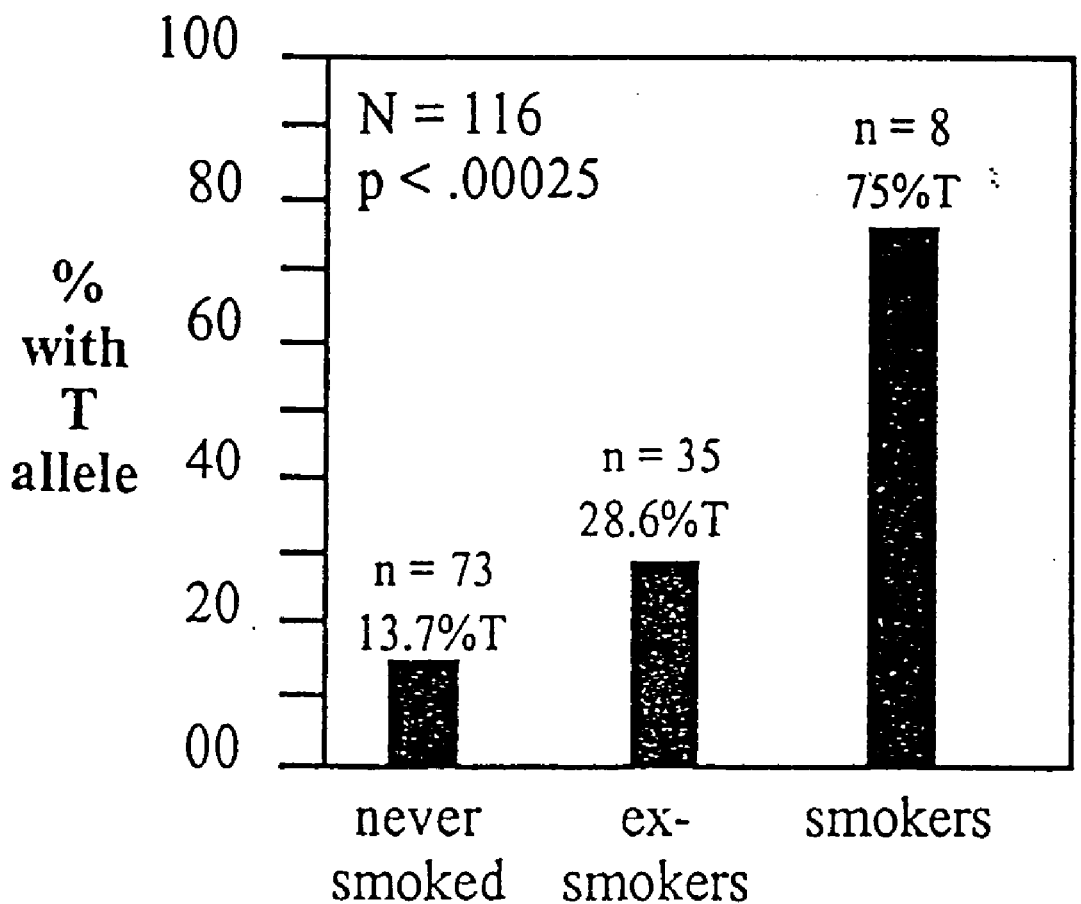
FIG. 1 depicts the relationship of the C-45T polymorphism of the CCK gene with smoking status in women.

There were 130 women in the study with an average age of 55.9 (S.D.=6.36). The mean BMI of the obese subjects was 38.88 (S.D. 7.97) and of the non-obese controls was 23.5 (S.D. 2.88). As shown in FIG. 1, 12.3% of women who never smoked carried the T allele. Carriers of the allele increased to 26.8% for women who smoked but had stopped, and to 75% for women who were unable to quit smoking, chi square=18.7, d.f.=2, $p \leq 0.00009$. The T allele was present in 34.7% of women who ever smoked (ex-smokers+smokers), chi square=9.26, d.f.=1, $p \leq 0.0023$. The frequency of the T allele was 0.0617 in women who never smoked and 0.1735 in women who ever smoked, chi square=8.19, d.f=1, p=0.0042. The frequency of the T allele was 0.375 in the current smokers. When compared to women who never smoked, chi square=17.45, d.f.=1, $p \leq 0.0001$, ANOVA showed that of the four factors analyzed (age, BMI, SCL-90 anxiety, SCL-90 depression), only the CCK gene (p<0.001) was significantly associated with smoking status. The results of ANOVA are shown in Table 1.

TABLE 1

ANOVA for Smoking Status versus CCK Genotype with Age, BMI, SCL-90 Anxiety and SCL-90 Depression as Covariates.

| Covariates | d.f. | F | p |
| --- | --- | --- | --- |
| Age | 1 | .715 | .583 |
| BMI | 1 | .405 | .526 |
| SCL-90 anxiety | 1 | 1.341 | .250 |
| SCL-90 depression | 1 | .050 | .824 |
| Main effects | | | |
| CCK | 1 | 14.275 | <.001 |
| Explained | 5 | 3.37 | .007 |

CCK is a satiety neuropeptide (Smith and Gibbs, 1994) and CCK agonists result in a decrease in food intake in animals and humans (Crawley and Corwin, 1994). There are two CCK receptors, A and B. The A receptors are associated with satiety and pancreatic enzyme secretion including insulin (Crawley and Corwing, 1994; Funakoshi, et al. 1994; and Jensen, et al. 1989). The B receptors are associated anxiety, both spontaneous and associated with withdrawal from drugs of abuse including nicotine (Costall, et al. 1991). Studies with CCK agonists indicate that a target site of action is in the periphery and an intact vagus nerve is required for CCK to reduce food intake (Crawley and Corwin, 1994). However, central sites such as the paraventricular nucleus of the hypothalamus and the nucleus tractus solitarius contribute to the pathway that mediates the effect of peripherally administered CCK on appetite. See Crawley and Corwin, 1994; Crawley and Schwaber, 1984; Edwards et al., 1986; Fuze et al., 1985. In this regard, it is of interest that exposure to cigarette smoke also produces increases in CCK levels in the paraventricular hypothalamic region (Fuze et al., 1985).

Figure 2:
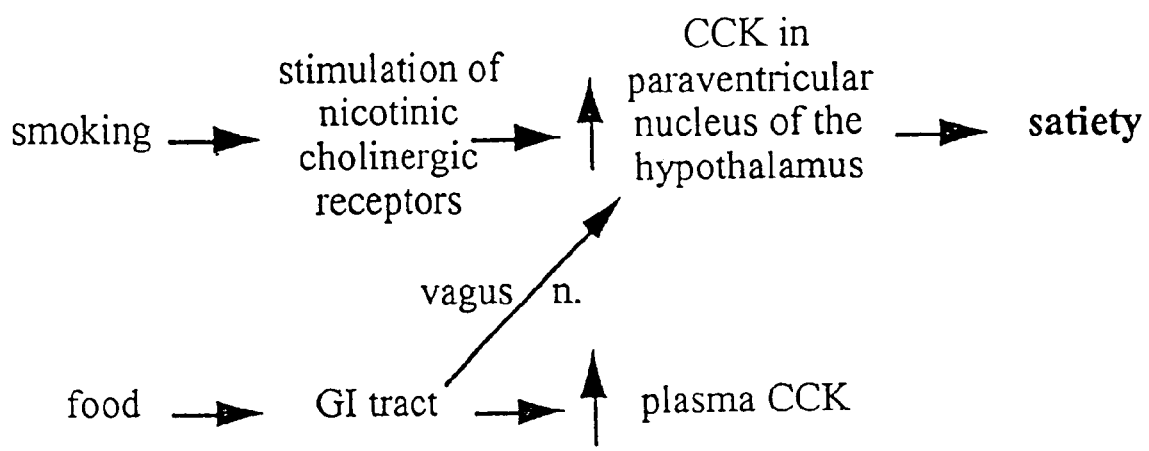
FIG. 2 depicts a possible model of the relationship between smoking and weight control.

These studies suggest that the stimulation of CCK production in the paraventricular hypothalamic region by nicotinic cholinergic receptors may be the mechanism by which smoking contributes to weight control. FIG. 2 presents a proposed model of the interactions between eating, satiety, smoking and weight control and suggests that CCK plays a central role in these interactions.

Twin studies of smoking have shown that while genetic factors contribute to approximately 50 percent of smoking initiation, they contribute to 70 percent of smoking persistence or resistance to smoking cessation (Heath and Martin, 1993; True et al., 1997), suggesting that genetic factors play a greater role in an inability to stop smoking than to start smoking. We propose that the present results are consistent with a role of genetic variants of the CCK gene as a risk factor for smoking, especially in women. Genetic variants of the CCK gene may also play a role in the relationship between smoking and weight control, and may help to explain why some individuals can stop smoking more readily than others. Collectively, these findings suggest that CCK acting agents may be useful aids for smoking cessation.

The present invention provides methods of screening the CCK gene to identify polymorphisms, particularly polymorphisms strongly associated with smoking in women. Such methods may further comprise the step of amplifying a portion of the gene, and may further include a step of providing a set of polynucleotides which are primers for amplification of said portion of the gene. The methods are useful for identifying polymorphisms for use in diagnosis and treatment of smoking.

The present invention provides the information necessary for physicians to select drugs for use in the treatment of smoking. With the discovery of the association of mutations in the CCK gene and smoking, drugs which are known CCK agonists can be selected for the treatment of smoking.

The present invention also provides a method for screening drug candidates to identify drugs useful for treating smoking. Drug screening is performed by comparing the activity of native genes and those described herein in the presence and absence of potential drugs.

The present invention further provides methods for genotyping individuals at risk for smoking. Such methods analyze the CCK gene for the polymorphisms described herein. The genotyping is particularly useful for testing potential drugs for effects on smoking cessation, those due to neuropeptide genes and those not due to neuropeptide genes. The genotyping can also include the identification of individuals who will respond to drugs that are agonists of CCK.

Proof that the CCK gene is involved as risk factor for smoking and unsuccessful smoking cessation in women is obtained by finding polymorphisms or sequences in DNA extracted from affected kindred members which create abnormal CCK gene products or abnormal levels of the gene products or which are statistically associated with smoking and/or unsuccessful smoking cessation in women. Such susceptibility alleles will co-segregate with the disease in large kindreds. They will also be present at a much higher frequency in non-kindred individuals who smoke and are unable to cease smoking than in individuals in the general population.

According to the diagnostic and prognostic method of the present invention, alteration of the wild-type CCK gene is detected. In addition, the method can be performed by detecting the wild-type CCK gene and confirming the lack of a risk factor for smoking and/or unsuccessful smoking cessation in women as a result of these loci. "Alteration of a wild-type gene" encompasses all forms of mutations including deletions, insertions and point mutations in the coding and noncoding regions, particularly those described herein. Deletions may be of the entire gene or of only a portion of the gene. Point mutations may result in stop codons, frameshift mutations or amino acid substitutions. Somatic mutations are those which occur only in certain tissues and are not inherited in the germline. Germline mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the CCK gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful are the recently developed techniques of mass spectroscopy (such as MALDI or MALDI-TOF; Fu et al. 1998) and DNA microchip technology for the detection of mutations.

The presence of a risk factor for smoking and unsuccessful smoking cessation in women may be ascertained by testing any tissue of a human for polymorphisms or mutations of the CCK gene. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for polymorphism or mutations of the CCK gene. Alteration of a wild-type CCK allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele-specific detection approach such as allele-specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of LQT cases. Southern blots displaying hybridizing fragments (differing in length from control DNA when probed with sequences near or including the CCK locus) indicate a possible mutation. If restriction enzymes which produce very large restriction fragments are used, then pulsed field gel electrophoresis (PFGE) is employed.

Detection of point mutations may be accomplished by molecular cloning of the CCK alleles and sequencing the alleles using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single-stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Ruano and Kidd, 1989). For allele-specific PCR, primers are used which hybridize at their 3' ends to a particular CCK polymorphism or mutation. If the particular polymorphism or mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type CCK gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the CCK gene can also be detected using Southern blot hybridization, especially if the changes are gross rearrangements, such as deletions and insertions.

DNA sequences of the CCK gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified CCK sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen individuals for mutations in the breast cancer gene BRCA1 (Hacia et al., 1996). This new technology has been reviewed in a news article in *Chemical and Engineering News* (Borman, 1996) and been the subject of an editorial (Editorial, Nature Genetics, 1996). Also see Fodor (1997).

The most definitive test for mutations in a candidate locus is to directly compare genomic CCK sequences from patients with those from a control population. Alternatively, one could sequence messenger RNA after amplification, e.g., by PCR, thereby eliminating the necessity of determining the exon structure of the candidate gene.

Mutations falling outside the coding region of CCK can be detected by examining the non-coding regions, such as introns and regulatory sequences near or within the genes. An early indication that mutations in non-coding regions are important may come from Northern blot experiments that reveal messenger RNA molecules of abnormal size or abundance in patients as compared to those of control individuals.

Alteration of CCK mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type protein. For example, monoclonal antibodies immunoreactive with CCK can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered protein can be used to detect alteration of the wild-type CCK gene. Functional assays, such as protein binding determinations, can be used. In addition, assays can be used which detect CCK biochemical function. Finding a mutant CCK gene product indicates alteration of a wild-type CCK gene.

A mutant CCK gene or corresponding gene products can also be detected in other human body samples which contain DNA, such as serum, stool, urine and sputum. The same techniques discussed above for detection of mutant genes or gene products in tissues can be applied to other body samples. By screening such body samples, a simple early diagnosis can be achieved for women with a risk factor for smoking and unsuccessful smoking cessation.

The primer pairs of the present invention are useful for determination of the nucleotide sequence of a particular CCK allele using PCR. The pairs of single-stranded DNA primers can be annealed to sequences within or surrounding the gene in order to prime amplifying DNA synthesis of the gene itself. A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular CCK polymorphic or mutant alleles, and thus will only amplify a product in the presence of the polymorphic or mutant allele as a template.

In order to facilitate subsequent cloning of amplified sequences, primers may have restriction enzyme site sequences appended to their 5' ends. Thus, all nucleotides of the primers are derived from the gene sequence or sequences adjacent the gene, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are coCCKrcially available. Given the sequence of each gene and polymorphisms described herein, design of particular primers is well within the skill of the art. The present invention adds to this by presenting data on the intron/exon boundaries thereby allowing one to design primers to amplify and sequence all of the exonic regions completely.

The nucleic acid probes provided by the present invention are useful for a number of purposes. They can be used in Southern blot hybridization to genomic DNA and in the RNase protection method for detecting point mutations already discussed above. The probes can be used to detect PCR amplification products. They may also be used to detect mismatches with the CCK gene or mRNA using other techniques.

The presence of an altered (or a mutant) CCK gene has been associated with a risk factor for smoking and unsuccessful smoking cessation in women. In order to detect a CCK gene polymorphism or mutation, a biological sample is prepared and analyzed for a difference between the sequence of the allele being analyzed and the sequence of the wild-type allele. Polymorphic or mutant alleles can be initially identified by any of the techniques described above. The polymorphic or mutant alleles are then sequenced to identify the specific polymorphism or mutation of the particular allele. Alternatively, polymorphic or mutant alleles can be initially identified by identifying polymorphic or mutant (altered) proteins, using conventional techniques. The alleles are then sequenced to identify the specific polymorphism or mutation for each allele. The polymorphisms or mutations, especially those statistically associated with a risk factor for smoking and unsuccessful smoking cessation in women, are then used for the diagnostic and prognostic methods of the present invention.

Definitions

The present invention employs the following definitions, which are, where appropriate, referenced to CCK.

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the CCK region are preferably complementary to, and hybridize specifically to, sequences in the CCK region or in regions that flank a target region therein. CCK sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al., 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the CCK polypeptide and fragments thereof or to polynucleotide sequences from the CCK region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the CCK polypeptide or fragment. Monoclonal antibodies may be made by injecting mice with the protein polypeptides, fusion proteins or fragments thereof. Monoclonal antibodies will be screened by ELISA and tested for specific immunoreactivity with CCK polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is in the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"CCK Allele" refers, respectively, to normal alleles of the CCK locus as well as alleles of CCK carrying variations that are associated with an inability to overcome nicotine addiction, particularly in women.

"CCK Locus", "CCK Gene", "CCK Nucleic Acids" or "CCK Polynucleotide" each refer to polynucleotides, all of which are in the CCK region, respectively, that are likely to be expressed in normal tissue, certain alleles of which are associated with a risk factor for smoking and unsuccessful smoking cessation in women. The CCK locus is intended to include coding sequences, intervening sequences and regulatory elements controlling transcription and/or translation. The CCK locus is intended to include all allelic variations of the DNA sequence.

These terms, when applied to a nucleic acid, refer to a nucleic acid which encodes a human CCK polypeptide, fragment, homolog or variant, including, e.g., protein fusions or deletions. The nucleic acids of the present invention will possess a sequence which is either derived from, or substantially similar to a natural CCK-encoding gene or one having substantial homology with a natural CCK-encoding gene or a portion thereof.

The CCK gene or nucleic acid includes normal alleles of the CCK gene, respectively, including silent alleles having no effect on the amino acid sequence of the NEP polypeptide as well as alleles leading to amino acid sequence variants of the CCK polypeptide that do not substantially affect its function. These terms also include alleles having one or more mutations which adversely affect the function of the CCK polypeptide. A mutation may be a change in the CCK nucleic acid sequence which produces a deleterious change in the amino acid sequence of the NEP polypeptide, resulting in partial or complete loss of CCK function, respectively, or may be a change in the nucleic acid sequence which results in the loss of effective CCK expression or the production of aberrant forms of the CCK polypeptide.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally-occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the CCK region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a CCK-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the CCK locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides.

"CCK protein" or "CCK polypeptide" refers to a protein or polypeptide encoded by the CCK locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native CCK sequence, preferably in excess of about 90%, and more preferably at least about 95% homologous. Also included are proteins encoded by DNA which hybridize under high or low stringency conditions, to CCK-encoding nucleic acids and closely related polypeptides or proteins retrieved by antisera to the CCK protein(s).

The CCK polypeptide may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the CCK polypeptide. Such polypeptides may have an amino acid sequence which differs from the wild-type by one or more of addition, substitution, deletion or insertion of one or more amino acids.

"Operably linked" refers to a juxtaposition wherein the components so described are in a relationship permitting them to function in their intended manner. For instance, a promoter is operably linked to a coding sequence if the promoter affects its transcription or expression.

The terms "peptide mimetic" or "mimetic" are intended to refer to a substance which has the essential biological activity of the CCK polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural CCK polypeptide.

"Probes". Polynucleotide polymorphisms associated with CCK alleles which are associated with an inability to overcome nicotine addiction are detected by hybridization with a polynucleotide probe which forms a stable hybrid with that of the target sequence, under stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out non-specific/ adventitious bindings, that is, which minimize noise. (It should be noted that, throughout this disclosure, if it is stated simply that "stringent" conditions are used, that it is meant to be read that "high stringency" conditions are used.) Since such indications identify neutral DNA polymorphisms as well as mutations, these indications need further analysis to demonstrate detection of a CCK susceptibility allele.

Probes for CCK alleles may be derived from the sequences of the CCK region, its cDNA, functionally equivalent sequences, or the complements thereof. The probes may be of any suitable length, which span all or a portion of the CCK region, and which allow specific hybridization to the region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding CCK are preferred as probes. This definition therefore includes probes of sizes 8 nucleotides through 6000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding CCK is present in a cell or tissue. The present invention includes all novel probes having at least 8 nucleotides, its complement or functionally equivalent nucleic acid sequences. The present invention does not include probes which exist in the prior art.

Similar considerations and nucleotide lengths are also applicable to primers which may be used for the amplification of all or part of the CCK gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 6000. The primers may also be used to determine whether mRNA encoding CCK is present in a cell or tissue. The present invention includes all novel primers having at least 8 nucleotides derived from the CCK locus for amplifying the CCK gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for CCK polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of CCK polypeptides. Immunological activities include both immunogenic function in a target immune system, as well as sharing of immunological epitopes for binding, serving as either a competitor or substitute antigen for an epitope of the CCK protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for CCK polypeptides or fragments thereof is described below.

The present invention also provides for fusion polypeptides, comprising CCK polypeptides and fragments. Homologous polypeptides may be fusions between two or more CCK polypeptide sequences or between the sequences of CCK and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield (1963).

"Protein purification" refers to various methods for the isolation of the CCK polypeptides from other biological material, such as from cells transformed with recombinant nucleic acids encoding CCK, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A CCK protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Identity means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Methods commonly employed to determine identity between two sequences include, but are not limited to those disclosed in *Guide to Huge Computers,* Martin J. Bishop, ed., Academic Press, San Diego, 1994, and Carillo, H., and Lipman, D. (1988). Preferred methods to determine identity are designed to give the largest match between the two sequences tested. Such methods are codified in computer programs. Preferred computer program methods to determine identity between two sequences include, but are not limited to, GCG program package (Devereux et al. (1984), BLASTP, BLASTN, FASTA (Altschul et al. (1990); Altschul et al. (1997)).

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type CCK nucleic acid or wild-type CCK polypeptide. The modified polypeptide will be substantially homologous to the wild-type CCK polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type CCK polypeptide. Alternatively, the similarity of function (activity) of the modified polypeptide may be higher than the activity of the wild-type CCK polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type CCK gene function produces the modified protein described above.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Recombinant or chemically synthesized nucleic acids or vectors, transformation or transfection of host cells, transformed or transfected host cells and polypeptides are produced using conventional techniques, such as described in U.S. Pat. Nos. 5,837,492; 5,800,998 and 5,891,628, each incorporated herein by reference.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. Several approaches for use in rational drug design include analysis of three-dimensional structure, alanine scans, molecular modeling and use of anti-id antibodies. These techniques are well known to those skilled in the art, including those described in U.S. Pat. Nos. 5,837,492; 5,800,998 and 5,891,628, each incorporated herein by reference.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing are generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process. A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to, or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an NEP or APN specific binding partner, or to find mimetics of the NEP or APN polypeptide.

Following identification of a substance which modulates or affects polypeptide activity, the substance may be further investigated. Furthermore, it may be manufactured and/or used in preparation, i.e., a manufacture or formulation, or a composition such as a medicament, pharmaceutical composition or drug. These may be administered to individuals.

In order to detect the presence of a CCK allele predisposing an individual to an inability to overcome nicotine addiction, a biological sample such as blood is prepared and analyzed for the presence or absence of susceptibility alleles of CCK. In order to detect the presence of an inability to overcome nicotine addiction or as a prognostic indicator, a biological sample is prepared and analyzed for the presence or absence of polymorphic or mutant alleles of CCK. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis. Suitable diagnostic techniques include those described herein as well as those described in U.S. Pat. Nos. 5,837,492; 5,800,998 and 5,891,628, each incorporated herein by reference.

Initially, the screening method involves amplification of the relevant CCK sequence. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of CCK. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection of the resulting hybrid, if any, is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105; and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al. (1986).

Two-step label amplification methodologies are known in the art. These assays work on the principle that a small ligand (such as digoxigenin, biotin, or the like) is attached to a nucleic acid probe capable of specifically binding CCK. Allele-specific probes are also contemplated within the scope of this example, and exemplary allele-specific probes include probes encompassing the predisposing mutations of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

The presence of an inability to overcome nicotine addiction can also be detected on the basis of the alteration of wild-type CCK polypeptide. Such alterations can be determined by sequence analysis in accordance with conventional techniques. More preferably, antibodies (polyclonal or monoclonal) are used to detect differences in, or the absence of CCK peptides. Techniques for raising and purifying antibodies are well known in the art, and any such techniques may be chosen to achieve the preparations claimed in this invention. In a preferred embodiment of the invention, antibodies will immunoprecipitate CCK proteins from solution as well as react with these proteins on Western or immunoblots of polyacrylamide gels. In another preferred embodiment, antibodies will detect CCK proteins in paraffin or frozen tissue sections, using immunocytochemical techniques.

Preferred embodiments relating to methods for detecting CCK or its polymorphisms/mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

According to the present invention, a method is also provided of supplying wild-type CCK function to a cell which carries a mutant CCK allele, respectively. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner. Conventional methods are employed, including those described in U.S. Pat. Nos. 5,837,492; 5,800,998 and 5,891,628, each incorporated herein by reference.

Alternatively, peptides which have CCK activity can be supplied to cells which carry a mutant or missing CCK allele. Protein can be produced by expression of the cDNA sequence in bacteria, for example, using known expression vectors. Alternatively, the polypeptide(s) can be extracted from polypeptide-producing mammalian cells. In addition, the techniques of synthetic chemistry can be employed to synthesize the protein. Any of such techniques can provide the preparation of the present invention which comprises the CCK protein. The preparation is substantially free of other human proteins. This is most readily accomplished by synthesis in a microorganism or in vitro. Active CCK molecules can be introduced into cells by microinjection or by use of liposomes, for example. Alternatively, some active molecules may be taken up by cells, actively or by diffusion. Conventional methods are employed, including those described in U.S. Pat. Nos. 5,837,492; 5,800,998 and 5,891,628, each incorporated herein by reference.

Animals for testing therapeutic agents or for developing animal and cellular models can be selected after mutagenesis of whole animals or after treatment of germline cells or zygotes. Such treatments include insertion of polymorphic/mutant CCK alleles, usually from a second animal species, as well as insertion of disrupted homologous genes. Alternatively, the endogenous CCK gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). These transgenic, transplacement and knock-out animals can also be used to screen drugs that may influence the biochemical, neuropathological, and behavioral parameters relevant to an inability to overcome nicotine addiction. Cell lines can also be derived from these animals for use as cellular models, or in drug screening. Conventional methods are employed, including those described in U.S. Pat. Nos. 5,837,492; 5,800,998 and 5,891,628, each incorporated herein by reference.

The identification of the association between the CCK gene polymorphism/mutations and smoking in women permits the early presymptomatic screening of individuals to identify those at risk for nicotine addiction or to identify the cause of such disorders. To identify such individuals, the alleles are screened as described herein or using conventional techniques, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele-specific oligonucleotide (ASO), dot blot analysis and PCR-SSCP analysis. Also useful is the recently developed technique of DNA microchip technology. Such techniques are described in U.S. Pat. Nos. 5,837,492; 5,800,998 and 5,891,628, each incorporated herein by reference.

Genetic testing will enable practitioners to identify individuals at risk for nicotine addiction or an inability to overcome nicotine addiction at, or even before, birth. Presymptomatic diagnosis will enable better treatment of these disorders, including the use of existing medical therapies. Genetic testing will also enable practitioners to identify individuals having diagnosed disorders those in which the diagnosis results from CCK. Genotyping of such individuals will be useful for (a) identifying subtypes of depression that will respond to drugs that inhibit CCK activity, (b) identifying subtypes of depression that respond well to placebos versus those that respond better to active drugs and (c) guide new drug discovery and testing. This genotyping is particularly useful, since 30% to 50% of antidepressant drug response results from a placebo response which may be caused by the present genes.

The CCK polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents; and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936. Standard techniques well known in the art or the techniques specifically described herein are utilized.

The invention having been described, it will be apparent to those skilled in the art that the same may be varied in many ways without departing from the spirit and scope of the invention. Any and all such modifications are intended to be included within the scope of the claims.

LIST OF REFERENCES

Altschul, S. F. et al. (1990). *J. Mol. Biol.* 215:403.
Altschul, S F, et al. (1997). *Nucl. Acids Res.* 25:3389–3402.
Anand, R (1992). *Techniques for the Analysis of Complex Genomes* (Academic Press).
Ausubel, F M, et al. (1992). *Current Protocols in Molecular Biology,* (John Wiley & Sons, New York, N.Y.).
Bartel, P L, et al. (1993). *Cellular Interactions in Development: A Practical Approach,* Oxford University Press, pp. 153–179.
Biocomputing: Informatics and Genome Projects, Smith, D. W., ed., Academic Press, Press, NY (1993).
Borman, S (1996). *Chemical & Engineering News,* December 9 issue, pp. 42–43.
Capecchi, M R (1989). *Science* 244:1288.
Cariello, N F (1988). *Am. J. Human Genetics* 42:726–734.
Carillo, H. and Lipman, D. (1988). *SIAM J. Applied Math.* 48:1073.
Centers for Disease Control and Prevention (1997). *MMWR Mortality Wkly Rpt* December 26 46(51):1217–20.
Chee, M, et al. (1996). *Science* 274:610–614.
Chevray, P M and Nathans, D N (1992). *Proc. Natl. Acad. Sci. USA* 89:5789–5793.
Chowdhury, P, et al. (1989). *Pharmacol. Biochem. Behav.* 33:591–594.
Chowdhury, P, et al. (1990). *Pancreas* 5:222–229.
Chowdhury, P, et al. (1991). *Regul. Pept.* 33:11–20.
Compton, J (1991). *Nature* 350:91–92.
*Computational Molecular Biology,* Lesk, A. M., ed., Oxford Univ. Press, NY (1988).
*Computer Analysis of Sequence Data,* Part I, Griffin, A. M., and Griffin, H. G., eds., Humana Press, NJ (1994).
Conner, B J, et al. (1983). *Proc. Natl. Acad. Sci. USA* 80:278–282.
Costall, B, et al. (1991). *Neuropeptides* 19 Suppl:65–73.
Cotten, M, et al. (1990). *Proc. Natl. Acad. Sci. USA* 87:4033–4037.
Crawley, J N and Corwin, R I (1994). *Peptides* 15:731–755.
Crawley, J N and Schwaber, J S (1984). *Brain Res.* 295:289–299.
Crisp, A, et al. (1999). *J. Adolesc.* 22:657–672.
DeRisi, J, et al. (1996). *Nat. Genet.* 14:457–460.
Deutscher, M (1990). *Meth. Enzymology* 182:83–89 (Academic Press, San Diego, Calif.).
Devereux, J et al. (1984). *Nucl. Acids Res.* 12(1):387.
Donehower, L A, et al. (1992). *Nature* 356:215.
Editorial (1996). *Nature Genetics* 14:367–370.
Edwards, G L, et al. (1986). *Am. J. Physiol.* 251:R971–R977.
Elghanian, R, et al. (1997). *Science* 277:1078–1081.
Fahy, E, et al. (1991). *PCR Methods Appl.* 1:25–33.
Fields, S and Song, O-K (1989). *Nature* 340:245–246.
Fink, H, et al. (1999). *Exp. Brain Res.* 123:77–83.
Finkelstein, J, et al. (1990). *Genomics* 7:167–172.
Fodor, S P A (1997). *Science* 277:393–395.
Fu, D-J., et al. (1998). *Nat. Biotechnol.* 16:381–384.
Funakoshi, A, et al. (1994). *Biochem. Biophys. Res. Commun.* 199:482–488.
Fuze, K, et al. (1985). *Acta Physiol Scand.* 125:437–443
Giovino G A, et al. (1995). *Epidemiol. Rev.* 17:48–65.
Glover, D (1985). *DNA Cloning,* I and II (Oxford Press).
Goding (1986). *Monoclonal Antibodies: Principles and Practice,* 2d ed. (Academic Press, NY).
Godowski, P J, et al. (1988). *Science* 241:812–816.
Grompe, M (1993). *Nature Genetics* 5:111–117.
Grompe, M, et al. (1989). *Proc. Natl. Acad. Sci. USA* 86:5855–5892.
*Guide to Huge Computers,* Martin J. Bishop, ed., Academic Press, San Diego, Calif. (1994).
Guthrie, G and Fink G R (1991). *Guide to Yeast Genetics and Molecular Biology* (Academic Press).

Hacia, J G, et al. (1996). *Nature Genetics* 14:441–447.
Harada, S, et al. (1998). *Alcholism: Clin. and Exp. Res.* 22:93S–96S.
Harlow, E and Lane, D (1988). *Antibodies: A Laboratory Manual* (Cold Spring Harbor Laboratory, Cold Spring Harbor, N.Y.).
Hasty, P K, et al. (1991). *Nature* 350:243.
Heath, A C and Martin, N G (1993). *Addictive Behaviors* 18:19–34.
Huse, W D, et al. (1989). *Science* 246:1275–1281.
Innis, M A, et al. (1990). *PCR Protocols: A Guide to Methods and Applications* (Academic Press, San Diego, Calif.).
Ishiguro, H, et al. (1999). *Psychiatry Res.* 85:209–213.
Jablonski, E, et al. (1986). *Nucl. Acids Res.* 14:6115–6128.
Jensen, R T, et al. (1989). *Trends Pharmacol. Sci.* 10:418–423.
Kanehisa, M (1984). *Nucl. Acids Res.* 12:203–213.
Kendrick, J S and Merritt, R K (1996). *Am. J. Obstet. Gynecol.* 175:528–535.
Kinszler, K W, et al. (1991). *Science* 251:1366–1370.
Klesges, R C, et al. (1999). *Ann. Behavioral Medicine* 11:134–143.
Kohler, G and Milstein, C (1975). *Nature* 256:495–497.
Kraemer, F B, et al. (1993). *J. Lipid Res.* 34:663–672.
Landegren, U, et al. (1988). *Science* 242:229–237.
Lee, J E, et al. (1995). *Science* 268:836–844.
Lipshutz, R J, et al. (1995). *BioTechniques* 19:442–447.
Lockhart, D J, et al. (1996). *Nature Biotechnology* 14:1675–1680.
Maniatis, T, et al. (1982). *Molecular Cloning: A Laboratory Manual* (Cold Spring Harbor Laboratory, Cold Spring Harbor, N.Y.).
Martin, R, et al. (1990). *BioTechniques* 2:762–768.
Matthews, J A and Kricka, L J (1988). *Anal. Biochem.* 169:1.
Merrifield, B (1963). *J. Am. Chem. Soc.* 85:2149–2156.
Mifflin, T E (1989). *Clinical Chem.* 35:1819–1825.
Modrich, P (1991). *Ann. Rev. Genet.* 25:229–253.
Mombaerts, P, et al. (1992). *Cell* 68:869.
Newton, C R, et al. (1989). *Nucl. Acids Res.* 17:2503–2516.
Nguyen, Q, et al. (1992). *BioTechniques* 13:116–123.
Novack, D F, et al. (1986). *Proc. Natl. Acad. Sci. USA* 83:586–590.
Orita, M, et al. (1989). *Proc. Natl. Acad. Sci. USA* 86:2766–2770.
Philpott, K L, et al. (1992). *Science* 256:1448.
*Remington's Pharmaceutical Sciences*, 18th Ed. (1990, Mack Publishing Co., Easton, Pa.).
Rasmussen K, et al. (1996). *Neuro Report* 10:1050–1052.
Rigby, P W J, et al. (1977). *J. Mol. Biol.* 113:237–251.
Ruano, G and Kidd, K K (1989). *Nucl. Acids Res.* 17:8392.
Sambrook, J, et al. (1989). *Molecular Cloning: A Laboratory Manual*, 2nd Ed. (Cold Spring Harbor Laboratory, Cold Spring Harbor, N.Y.).
Scharf, S J, et al. (1986). *Science* 233:1076–1078.
Scopes, R (1982). *Protein Purification: Principles and Practice*, (Springer-Verlag, NY).
*Sequence Analysis in Molecular Biology*, von Heinje, G., Academic Press (1987).
*Sequence Analysis Primer*, Gribskov, M. and Devereux, J., eds., M Stockton Press, NY (1991)
Sheffield, V C, et al. (1989). *Proc. Natl. Acad. Sci. USA* 86:232–236.
Shenk, T E, et al. (1975). Proc. Natl. Acad. Sci. USA 72:989–993.
Shinkai, Y, et al. (1992). *Cell* 68:855.
Shoemaker, D D, et al. (1996). *Nature Genetics* 14:450–456.
Smith, G P and Gibbs, J (1994). *Ann. N.Y. Acad. Sci.* 1994; 713:236–41.
Snouwaert, J N, et al. (1992). *Science* 257:1083.
Sorensin, G, and Pechacek, T F (1987). *J. Behav. Med.* 10:129–137.
Spargo, C A, et al. (1996). *Mol. Cell. Probes* 10:247–256.
Steer, R A, et al. (1994). *J. Pers. Assess.* 62:525–536.
True, W R, et al. (1997). *Addiction* 92:1277–1287.
Valancius, V and Smithies, O (1991). *Mol. Cell Biol.* 11:1402.
Walker, G T, et al. (1992). *Nucl. Acids Res.* 20:1691–1696.
Wang, Z, et al. (1998). *Am. J. Medical Genetics* 81:228–234.
Wartell, R M, et al. (1990). *Nucl. Acids Res.* 18:2699–2705.
Wetmur, J G and Davidson, N (1968). *J. Mol. Biol.* 31:349–370.
White, M B, et al. (1992). *Genomics* 12:301–306.
White, R and Lalouel J M (1988). *Annu. Rev. Genet.* 22:259–279.
Winders, S E and Grunberg, N E (1989). *Ann. Behavioral Medicine* 11:125–133.
Wu, D Y and Wallace, R B (1989). *Genomics* 4:560–569.
Patents and Patent Applications:
European Patent Application Publication No. 0332435.
EPO Publication No. 225,807.
EP 425,731A.
WO 90/07936.
WO 92/19195.
WO 94/25503.
WO 95/01203.
WO 95/05452.
WO 96/02286.
WO 96/02646.
WO 96/11698.
WO 96/40871.
WO 96/40959.
WO 97/12635.
U.S. Pat. No. 3,817,837.
U.S. Pat. No. 3,850,752.
U.S. Pat. No. 3,939,350.
U.S. Pat. No. 3,996,345.
U.S. Pat. No. 4,275,149.
U.S. Pat. No. 4,277,437.
U.S. Pat. No. 4,366,241.
U.S. Pat. No. 4,376,110.
U.S. Pat. No. 4,486,530.
U.S. Pat. No. 4,683,195.
U.S. Pat. No. 4,683,202.
U.S. Pat. No. 4,816,567.
U.S. Pat. No. 4,868,105.
U.S. Pat. No. 5,270,184.
U.S. Pat. No. 5,409,818.
U.S. Pat. No. 5,455,166.
U.S. Pat. No. 5,550,050.
U.S. Pat. No. 5,800,998.
U.S. Pat. No. 5,837,492.
U.S. Pat. No. 5,891,628.

What is claimed is:

1. A method for screening a female subject to determine whether said subject is at risk for nicotine dependence or unsucessful cessation of smoking, which comprises determining whether the subject has a T at position −45 of the cholecystokinin gene, wherein the presence of a T at position −45 of the cholecystokinin gene correlates with a risk for nicotine dependence or unsuccessful cessation of smoking.

2. The method of claim 1, wherein the determining step comprises a hybridization reaction.

3. The method of claim 2, wherein the determining step reaction comprises fluorescence in situ hybridization.

4. The method of claim 1, wherein the determining step comprises DNA sequencing.

5. The method of claim 1, wherein the determining step comprises PFGE analysis.

6. The method of claim 1, wherein the determining step comprises Southern blot analysis.

7. The method of claim 1, wherein the determining step comprises a single stranded conformation analysis.

8. The method of claim 1, wherein the determining step comprises an RNase protection assay.

* * * * *